US006974409B2

(12) United States Patent
Verkerke et al.

(10) Patent No.: US 6,974,409 B2
(45) Date of Patent: *Dec. 13, 2005

(54) CATHETER PUMP, CATHETER AND METHOD FOR SUPPORTING ORGAN PERFUSION

(75) Inventors: Gijsbertus Jacob Verkerke, Haren (NL); Arjan van der Plaats, Groningen (NL); Gerhard Rakhorst, Groningen (NL)

(73) Assignee: Intra-Vasc.NL B.V., Groningen (NL)

( * ) Notice: Subject to any disclaimer, the term of this patent is extended or adjusted under 35 U.S.C. 154(b) by 210 days.

This patent is subject to a terminal disclaimer.

(21) Appl. No.: 10/072,348

(22) Filed: Feb. 7, 2002

(65) Prior Publication Data

US 2002/0123661 A1 Sep. 5, 2002

Related U.S. Application Data

(63) Continuation-in-part of application No. 09/363,711, filed on Jul. 29, 1999, now Pat. No. 6,398,714.

(51) Int. Cl.[7] .............................................. A61M 1/12
(52) U.S. Cl. ......................................................... 600/16
(58) Field of Search .................................... 600/16–18

(56) References Cited

U.S. PATENT DOCUMENTS

| 3,592,184 A | * | 7/1971 | Watkins et al. |
| 3,995,617 A | | 12/1976 | Watkins et al. |
| 4,014,317 A | | 3/1977 | Bruno |
| 6,007,479 A | | 12/1999 | Rottenberg et al. |

FOREIGN PATENT DOCUMENTS

| FR | 2 144 806 | 2/1973 |
| GB | 1370546 | 10/1974 |
| GB | 1528072 | 10/1978 |
| WO | WO 97/02850 | 1/1977 |
| WO | WO 89/10763 | 11/1989 |
| WO | WO 98/57698 | 12/1998 |
| WO | WO 99/26676 | 6/1999 |

OTHER PUBLICATIONS

Gary S. Allen, Kevin D. Murray and Don B. Olsen, "The Importance of Pulsatile and Nonpulsatile Flow in the Design of Blood Pumps", 1997, Artificial Organs 21(8), pp. 922-928.

Andrew J. Lodge, Akif Undar, C. William Daggett, Thomas M. Runge, John H Calhoon and Ross M. Ungerleider, "Regional Blood Flow During Pulsatile Cardiopulmonary Bypass and After Circulatory Arrest in an Infant Model", 1997, Ann Thorac Surg 1997;63, pp. 1243-1250.

(Continued)

Primary Examiner—Scott M. Getzow
(74) Attorney, Agent, or Firm—Pearne & Gordon LLP

(57) ABSTRACT

A catheter pump includes a displacement structure and a catheter. The catheter has an inlet in its distal end portion and an outlet spaced from the distal end portion. The displacement structure alternatingly applies suction for displacing fluid from the catheter to the displacement structure and pressure for displacing fluid from the displacement structure to the catheter. By inserting a distal end portion of the catheter into the aorta, pulsations can be applied to the blood pressure in the aorta. By applying pulsations, perfusion of the organs can be improved.

17 Claims, 5 Drawing Sheets

OTHER PUBLICATIONS

Akira Sezai, Motomi Shiono, Yukihiko Orime, Kin-ichi Nakata, Mitsumasa Hata, Mitsuru Iida, Satoshi Kashiwazaki, Jun-ichi Kinoshita, Mitsuhiro Nemoto, Takashi Koujima, Motohiko Furuichi, Kunihiro Eda, Hiroyuki Hirose, Takanori Yoshino, Akira Saitoh, Yoshiki Taniguchi, and Yukiyasu Sezai, "Major Organ Function Under Mechanical Support: Comparative Studies of Pulsatile and Nonpulsatile Circulation", 1999, Artificial Organs 23(3), pp. 280-285.

Akif Undar, Takafumi Masai, Shuang-Qiang Yang, Jan Goddard-Finegold, O.H. Fraizer, and Charles D. Fraser, Jr., "Effects of Perfusion Mode on Regional and Global Organ Blood Flow in a Neonatal Piglet Model", 1999, Ann Thorac Surg; 68, pp. 1336-1343.

Yukihiko Orime, Motomi Shiono, Hiroaki Hata, Shinya Yagi, Saeki Tsukamoto, Haruhiko Okumura, Kin-ichi Nakata, Shun-ichi Kimura, Mitsumasa Hata, Akira Sezai and Yukiyasu Sezai, "Cytokine and Endothelial Damage in Pulsatile and Nonpulsatile Cardiopulmonary Bypass", 1999, Artificial Organs; 23(6), pp. 508-512.

* cited by examiner

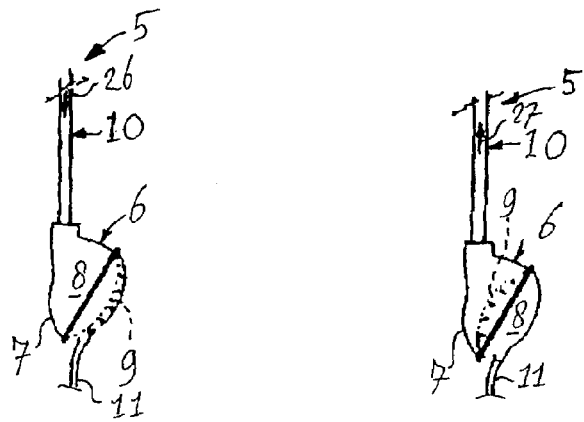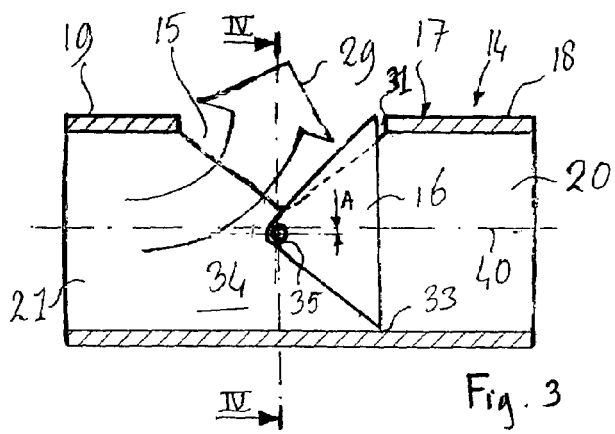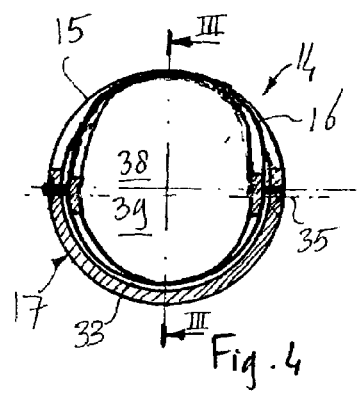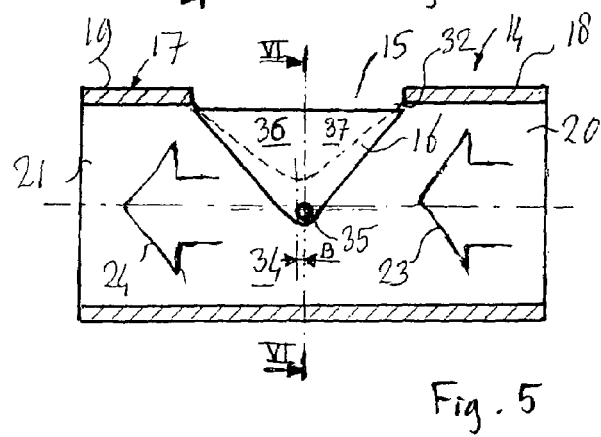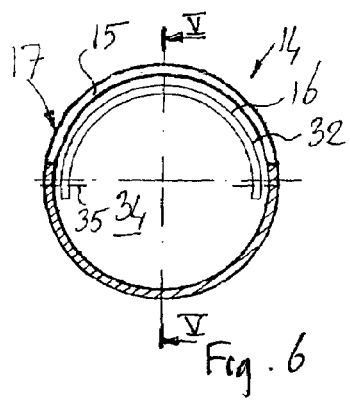

CATHETER PUMP, CATHETER AND METHOD FOR SUPPORTING ORGAN PERFUSION

This application is a continuation-in-part of application Ser. No. 09/363,711, filed Jul. 29, 1999, now U.S. Pat. No. 6,398,714.

TECHNICAL FIELD

The invention relates to a catheter pump, to a catheter, and to a method for supporting blood transport within a human body using such a catheter.

BACKGROUND ART

From U.S. Pat. No. 3,995,617 a heart assist catheter pump is known which includes a catheter having a distal end for insertion from the aorta past the aortic valve into the left ventricle. The distal end has inlet openings and a check valve for allowing inward flow. Spaced from the distal end, the catheter has outlet openings and a set of second check valves for allowing outward flow. A pump device communicating with the proximal end of the catheter alternatingly generates a suction causing blood to be withdrawn from the left ventricle into the catheter and to the pump device and an excess pressure causing blood to be reintroduced via the set of second check valves into the heart on the downstream side of the aortic valve. The second check valves are each formed by an elastic booth at the outside of the catheter.

Other examples of such a catheter pump for assisting the heart are known from U.S. Pat. Nos. 4,014,317 and 6,007,479.

During open heart surgery on an inactive heart, in practice blood circulation is usually maintained using a heart lung machine including a pump and an oxygenator. The pump is usually a non-pulsatile pump, which provides advantages in terms of design and compatibility with the function of the oxygenator (Allen et al.; "The importance of Pulsatile and Nonpulsatile Flow in the Design of Blood Pumps"; Artificial Organs 21(8): 922–928).

On the other hand, organ failure after open-heart surgery is a frequent cause of complications. Different theories regarding the causes of such organ failure exist. One of these theories is, that the use of a heart-lung machine has several side effects that may influence blood pressure and organ perfusion. For example, the heart-lung machine indices (a) a non-physiological (non-pulsatile) flow pattern, (b) a decreased blood viscosity when the priming liquid from the tubing and the oxygenator is introduced into the patient's blood circulation, (c) unwanted blood-material interactions. Reduced blood pressure can lead to reduced abdominal organ perfusion, which in turn can cause reduced organ functions. Other instances when reduced blood pressure may disturb organ functions are: during toxic shock, which may for instance be caused by an allergic reaction and, prolonged cardiac malfunction, which frequently entails multi-organ failure.

Several research results indicate that a pulsatile flow is advantageous for obtaining sufficient blood flow to the organs. For instance, pulsatile flow in a cardio pulmonary bypass has been found to have a positive effect on the blood flow rate to the kidneys of neonate pigs (Lodge et al.; "Regional Blood Flow During Pulsatile Cardiopulmonary Bypass and After Circulatory Arrest in an Infant Model"; Ann Thorac Surg 1997; 63:1243–50).

During an acute heart attack of a pig, blood flow to the liver and to the kidneys and microcirculation at cellular level were found to be improved if during three hour biventricular cardiac assist, the flow was pulsatile (Sezai et al.; "Major Organ Function Under Mechanical Support: Comparative Studies of Pulsatile and Nonpulsatile Circulation"; Artificial Organs 1999; 23(3): 280–285). During left ventricle cardiac assist in a similar situation, pulsatile cardiac assist provided superior circulation in the liver and superior microcirculation on a cellular level, at least in the initial phase of the treatment after the heart attack.

During open-heart surgery on neonate pigs, a positive effect of pulsatile flow on the blood flow to the organs, the brain and the heart muscles was found (Ündar et al.; "Effects of Perfusion Mode on Regional and Global Organ Blood Flow in a Neonatal Piglet Model"; Ann Thorac Surg; 68: 1336–43).

In clinical Cardiopulmonary Bypass cases, the results of measurement of cytokine, endothelium and other metabolic parameters indicated that the damage to the endothelium was less and the cytokine activation was reduced in a patient group treated with a pulsatile flow compared with another group treated with a non pulsatile flow (Orime Y. et al., "Cytokine and Endothelial Damage in Pulsatile and Non-pulsatile Cardiopulmonary Bypass"; Artificial Organs 1999; 23(6):508–512).

SUMMARY OF THE INVENTION

It is an object of the invention to provide a simple but effective solution improving organ perfusion of a patient in a state of unwanted hypotension.

According to the invention, this object is achieved by providing a catheter pump including:

a catheter having a distal end portion and a proximal end portion, a channel communicating with the distal end portion for alternatingly passing a fluid in a direction away from the distal end portion towards the proximal end portion and in a direction away from the proximal end portion towards the distal end portion;

a connection at the proximal end for coupling the catheter to a displacement structure; and a displacement structure;

the displacement structure communicating with the catheter for alternatingly applying suction for displacing fluid from the catheter to the displacement structure and applying pressure for displacing fluid from the displacement structure to the catheter; and the catheter being dimensioned for positioning the distal end portion in the aorta of a human patient.

Using such a catheter pump, pulsatile pressure variations applied by a displacement structure connected to the proximal end of the catheter can be transferred into the aorta, so that pulsatile pressure variations are introduced into the blood flow towards at least one of the organs.

The invention further provides a catheter having a distal end portion and a proximal end portion, a channel communicating with the distal end portion for alternatingly passing a fluid in a direction away from the distal end portion towards the proximal end portion and in a direction away from the proximal end portion towards the distal end portion; and a connection at the proximal end for coupling the catheter to a displacement structure for alternatingly applying suction for displacing fluid from the catheter to the displacement structure and applying pressure for displacing fluid from the displacement structure to the catheter;

the catheter being dimensioned for positioning the distal end portion in the aorta of a human patient.

The displacement structure can for instance include a drive structure, such as an electric motor. The displacement structure can also include a transmission such as a membrane element for transmitting displacement of a transfer fluid to a fluid in the catheter.

Furthermore, the invention provides a method for generating pulsations in the blood flow towards the organs of a human patient including:

inserting a catheter into the aorta of a patient and bringing the catheter in a position having a distal end portion in the aorta of the patient; and alternatingly withdrawing a fluid from the aorta and feeding a fluid to the aorta via the catheter, such that pressure pulsations are generated in an area of the aorta where the distal end portion of the catheter is located.

Further objects, features, effects, advantages and details of the invention are described with reference to examples shown in the drawings.

BRIEF DESCRIPTION OF THE DRAWINGS

FIGS. 1 and 2 show proximal end portions of a catheter pump according to the invention;

FIG. 3 is a side view in cross-section along the line III—III in FIG. 4 of a fitting according to the invention;

FIG. 4 is a side in cross-section along the line IV—IV in FIG. 3;

FIG. 5 is a side view in cross-section along the line V—V in FIG. 6 of the fitting according to FIGS. 3 and 4 in a different operating condition;

FIG. 6 is a side in cross-section along the line VI—VI in FIG. 5;

DETAILED DESCRIPTION

Figure 9:
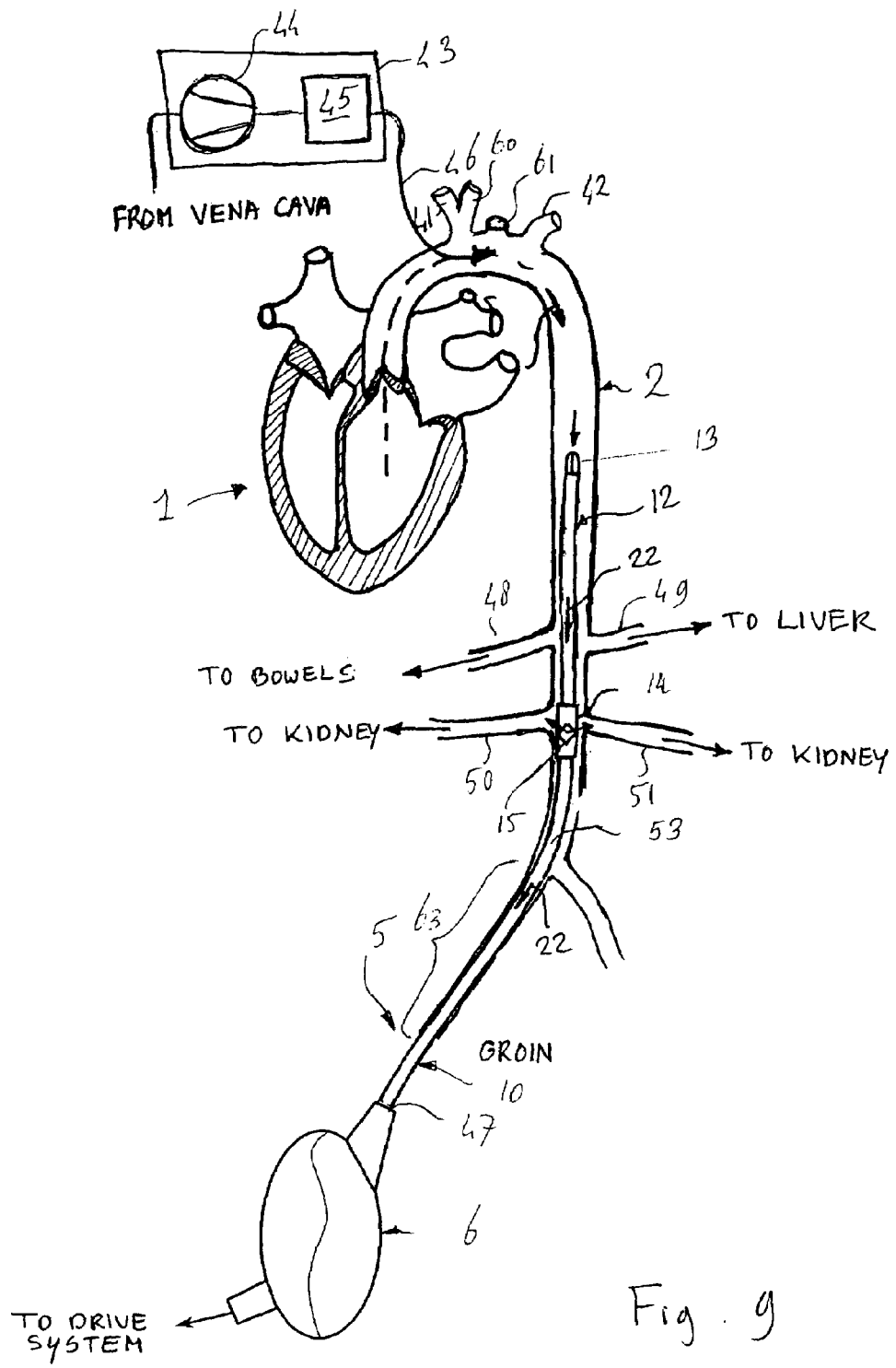
FIGS. 9–11 are schematic representations of treatment of the blood pressure in the aorta using different embodiments of a catheter pump as proposed.
Figure 10:
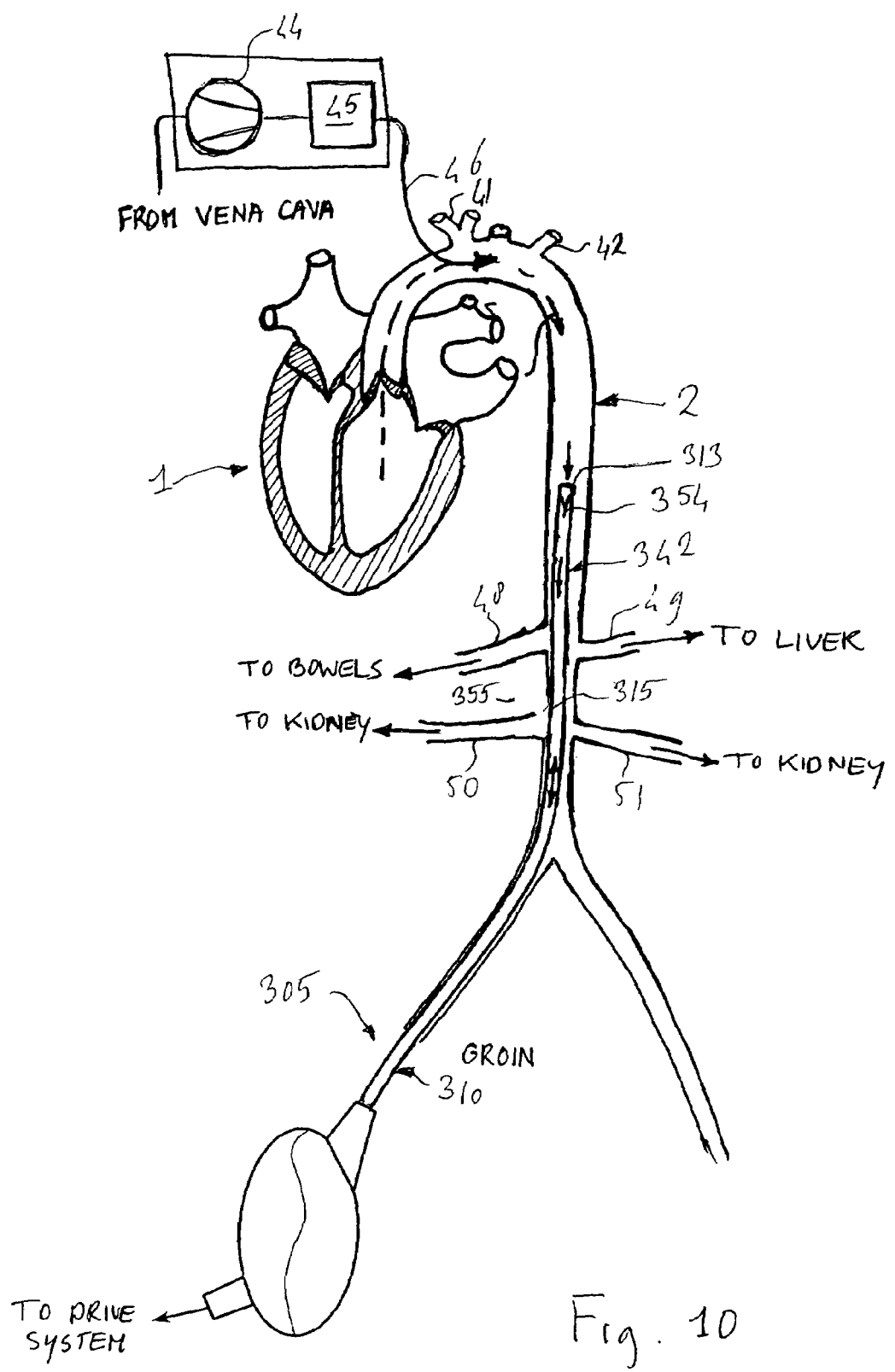
Figure 11:
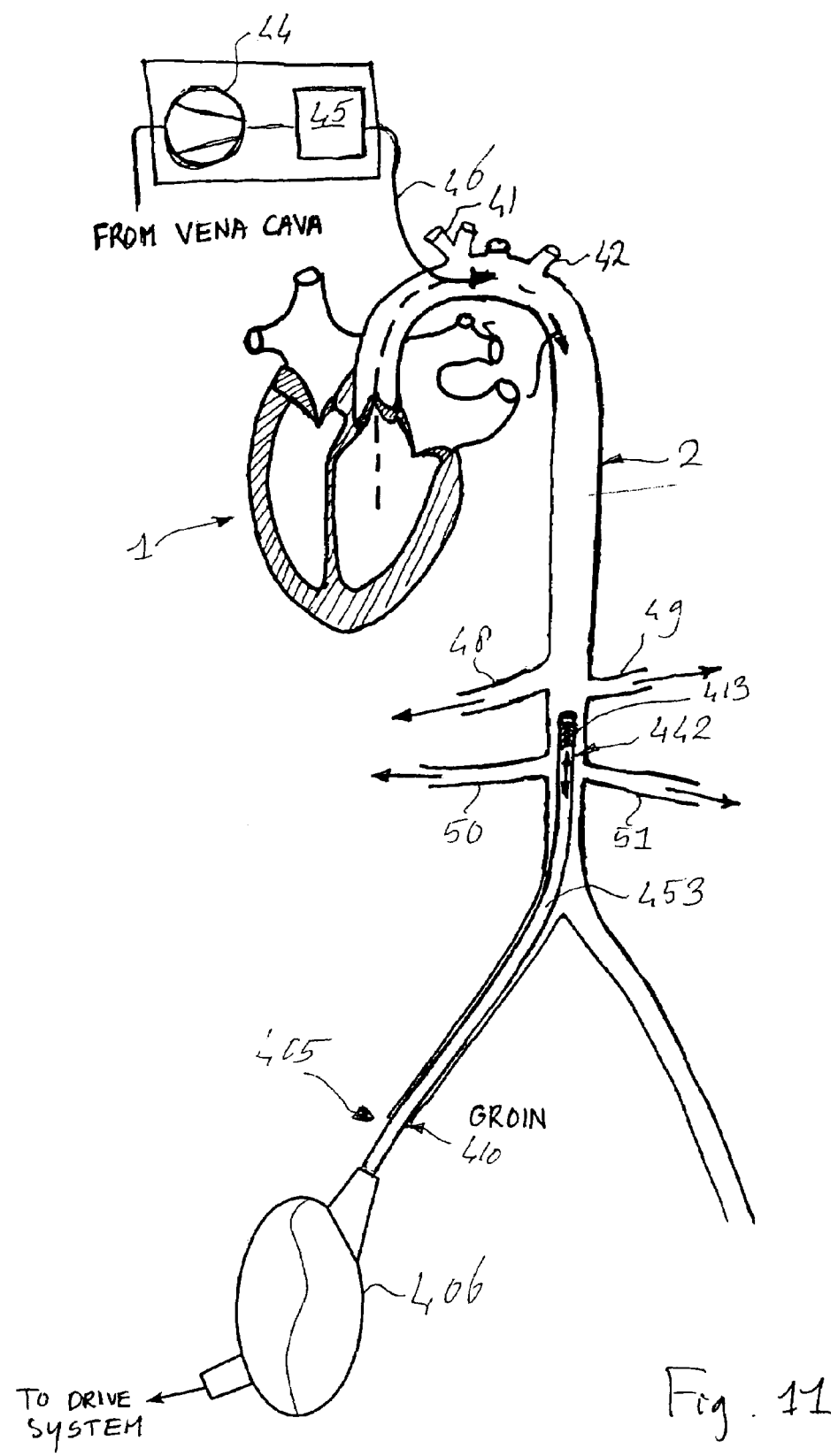

In FIGS. 9–11 a heart 1 and an aorta 2 connected thereto are depicted. The heart has a left ventricle 3 and an aortic valve 4. FIGS. 1 and 2 show a catheter pump in use in a different treatment than the treatment proposed in the present application. However, in a suitably adapted form, the shown and described catheter and catheter pump can also be used for the proposed treatment for generating pulsations in the blood flow in the aorta.

Referring to FIGS. 1, 2 and 9, the pulsatile catheter pump 5 has a displacement device 6 in the form of a rigid housing 7 enclosing a chamber 8 divided by a flexible membrane 9. The catheter pump 5 further has a catheter 10 projecting from that displacement device 6 and communicating with a portion of the chamber 8 on a distal side of the membrane 9 and a pneumatic conduit 11 communicating with a pump drive unit (not shown) and with a portion of the chamber 8 on a proximal side of the membrane 9. The displacement structure 6 can be driven via the pneumatic conduit 11 for alternatingly applying suction for displacing fluid from the catheter 10 to the displacement structure 6 and for applying pressure for displacing fluid from the displacement structure 6 to the catheter 10, thus driving a flow through the catheter 10 which reverses in a pulsating manner.

The catheter 10 projects from the displacement device 6 into the aorta 2 via an artery 52 in the area of the groin.

A distal end portion 12 of the catheter 10 is provided with inlet passages 13. Spaced in proximal direction from the inlet passages 13, the catheter 10 is provided with a fitting 14 having an outlet passage 15.

The fitting 14 is shown in more detail in FIGS. 3–6. The catheter pump, the catheter and the fitting as shown in FIGS. 1–6 and 9 represent the presently most preferred embodiment of the invention.

The fitting 14 has a tube shaped housing 17. In this example, the housing has a circular cross-section, but other cross-sectional shapes are conceivable as well.

The fitting 14 further has a coupling 18 for coupling to a distal portion 12 of the catheter 10 on one end and a coupling 19 for coupling to a proximal portion of the catheter 10 on its opposite end. The representation in the drawings of the couplings 18, 19 for coupling to the catheter 10 is of a schematic nature. The couplings are preferably made as is described in International patent application WO 97/18936.

The fitting 14 has three passages. A first passage 20 through the coupling 18 for coupling to the distal portion of the catheter 10, a second passage 21 through the coupling 19 for coupling to a proximal portion of a catheter 10 and a third passage communicating with the first and second passages 20, 21 which is formed by the opening 15.

The fitting 14 is further provided with a valve arrangement for blocking outward blood flow via the inlet passages 13 and inward blood flow via the outlet passage 15. The valve arrangement is formed by a valve body 16 movable between an inlet position substantially obstructing, or at least restricting flow through the outlet passage 15—i.e. the third passage of the fitting 14—and allowing flow through the inlet passage 13 and the first passage 20 of the fitting 14 (FIGS. 5 and 6) and an outlet position substantially obstructing, or at least restricting flow through the inlet passage 13 and the first passage 20 of the fitting 14 and allowing flow through the outlet passage 15 (FIGS. 3 and 4).

Although it would in principle be possible to control the motions of the valve body 16 actively in accordance with operation of the pump drive unit, it is preferred to control the motions of the valve body 16 passively, such that the valve body 16 is movable from the inlet position (FIGS. 5 and 6) to the outlet position (FIGS. 3 and 4) in response to pressure applied by the displacement structure 6 to and via the second passage 21 and is movable from the outlet position to the inlet position in response to suction applied by the displacement structure 6 to and via the second passage 21. Thus, the need of providing a drive unit and provisions for feeding power to the drive unit are avoided, and the costs and complexity of the construction are reduced while the reliability is improved.

In operation, when the displacement device 6 pulls blood via the catheter 10, the valve body 16 is urged into the position shown in FIGS. 5 and 6 which causes blood to be withdrawn from the aorta 2 and through the catheter 10 as is indicated by arrows 22–24 and 26 shown in FIGS. 1, 5, 6 and 9. After the desired volume of blood for the support of one stroke has been collected, the pump drive unit is controlled to reverse from withdrawing air form the chamber 8 to pressing air into the chamber 8. In response, blood is pressed into the catheter 10 and the blood flow in the catheter 10 is reversed as is indicated by the arrow 27 in FIG. 2. In response to the reversal of the blood flow, the valve member 16 is urged from the inlet position shown in FIGS.

5 and 6 into the outlet position shown in FIGS. 3 and 4. This causes the blood flow to be prevented from flowing back through the first passage 20 and the inlet openings 13 possibly apart from some leakage) and to be forced out of the catheter 10 via the outlet opening 15 in an upstream portion of the aorta 2, as is indicated by arrow 29 in FIG. 3.

Since the valve body 16 is located inside the catheter 10, the valve body 16 does not increase the cross-section of the catheter 10, which is advantageous for facilitating insertion of the catheter 10 and to avoid causing damage to tissue of the patient as small as possible. Furthermore, the risk of damaging the valve is reduced as well.

In each operating condition, interspaces 31, 32, 33 between the valve body 16 and the wall 30 of the fitting 14 are each open on at least two opposite sides for allowing blood flow through the interspaces. This counteracts the formation of stagnation zones where blood is prone to clot. Thus the risk of the formation of thromboses at the valve is further reduced. Thrombogenetic blood flow stagnation zones are further counteracted since the valve body 16 allows some leakage (about 5%), so that in each operating condition the interspaces are flushed due to the pressure drop over the valve body 16.

In the particular example shown in FIGS. 3–6, the housing wall 17 of the fitting 14 of the catheter 10 bounds a lumen 34 and the outlet opening 15 is formed by a passage in the wall 17.

The valve body 16 is formed by a plate-shaped member, which extends closely along and inside an axial projection of the wall 17 in the area of the opening 15 when in the inlet position shown in FIGS. 5 and 6. When in the outlet position shown in FIGS. 3 and 4, the valve body 16 extends transversely across a section of the lumen 34 on a distal side of the outlet opening 15. The valve body 16 is pivotable between the inlet position and the outlet position about an axis 35 extending across a central portion of the lumen 34 and centrally located behind the opening 15.

When the blood flow through the catheter 10 is directed towards the proximal end, the drag caused by the flow retains the valve body 16 in the position shown in FIGS. 5 and 6. To prevent the valve body 16 from pivoting past the position in front of the opening 15, in this example a distal edge portion of the valve body 16 is in abutment with a portion of the wall 17 of the fitting 14 bounding a distal side of the opening 15. A particular advantage of this embodiment is, that the pressure in the aorta 2 does not tend to press the valve body 16 away from its position occluding the opening 15, because resulting torques caused by pressure in the aorta 2 higher than pressure in the lumen 34 essentially cancel each other out.

When the flow is reversed, the forces exerted onto valve body 16 by the drag of the blood flow are inverted, which causes the valve body 16 to be entrained to the outlet position shown in FIGS. 3 and 4.

When the blood flow is reversed again, the valve body 16 is entrained back to the inlet position shown in FIGS. 5 and 6.

In the present example, the lumen 34 has a circular cross-section. Like other round cross-sections, such as oval cross-sections, a circular cross-section provides the advantage of smoothness, which helps to prevent damage to vessels and other tissue of the patient.

The opening 15 is round in a view frontal thereto and wedge-shaped in a side view perpendicular to that frontal view, and the plate-shaped member is curved about axes of curvature transverse to the pivoting axis 35, round in frontal view and wedge-shaped in a side view perpendicular thereto. This allows a very large opening in the wall 17 of the fitting 14 to be alternatingly occluded and cleared by a valve body 16, which simultaneously clears, respectively occludes the round lumen 34 when in the outlet position extending transversely across the lumen 34.

The opening 15 provided according to the present example is particularly large, because, in side view, opposite sides of the wedge shapes of the opening and of the valve body extend approximately perpendicular to each other, for instance at an angle of 75–105° and preferably about 90° to each other.

In the inlet position, the valve body 16 has a frontal projected area having a portion 36 on a proximal side of the pivoting axis 35 and a portion 37 on a distal side of the axis 35. The portion 36 on the proximal side of the pivoting axis 35 is larger than the portion 37 on the distal side of the pivoting axis 35. This causes a pressure drop over the valve body 16 from the aorta 2 to the lumen 34 to assist retaining the valve body 16 in the inlet position. Conversely, if the pressure drop over the valve body 16 is inverted due to the reversal of the operation of the displacement device 6, this feature supports a quick movement of the valve body 16 out of the inlet position.

As appears particularly clearly from FIG. 4, in the outlet position, the valve body 16 has a frontal projected area having a portion 38 on a side of the pivoting axis 35 where the opening 15 is located and a portion 39 on an opposite side of the pivoting axis 35. The portion 38 on the side of the pivoting axis 35 where the opening 15 is located is larger than the portion 39 on the opposite side of the pivoting axis 35. This difference between the sizes of the frontal area portions 38, 39 on opposite sides of the pivoting axis 35 causes the valve body to be firmly urged into and retained in the outlet position by a pressure drop over the valve body 16 from the proximal side to the distal side as occurs during the outflow of blood under influence of pressure exerted by the displacement device 6. Conversely, if the pressure drop over the valve body 16 is inverted due to the reversal of the operation of the displacement device 6, this feature supports a quick movement of the valve body out of the outlet position.

For the same purpose, the portion of the cross section of the lumen 34 on the side of the pivoting axis 35 where the opening 15 is located is larger than the portion of the cross section of the lumen 34 on the opposite side of that pivoting axis 35.

In the present example, the desired difference in size between the projected frontal area portions 36 and 37 as well as 38 and 39 is obtained by providing that the location of the pivoting axis 35 is on the one hand offset from the central axis 40 of the lumen 34 in a direction away from the opening 15 and on the other hand offset from the center of the opening 15 in a distal direction. These offsets are indicated by reference mark A in FIG. 3 and, respectively, reference mark B in FIG. 4.

Figure 7:
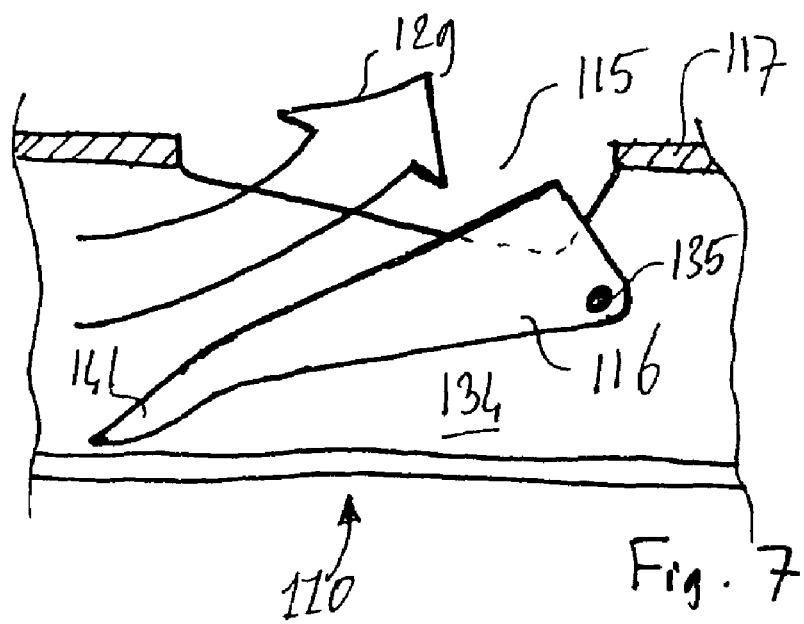
FIG. 7 is a side view in longitudinal cross-section of a section of a catheter according to another embodiment of the invention.
Figure 8:
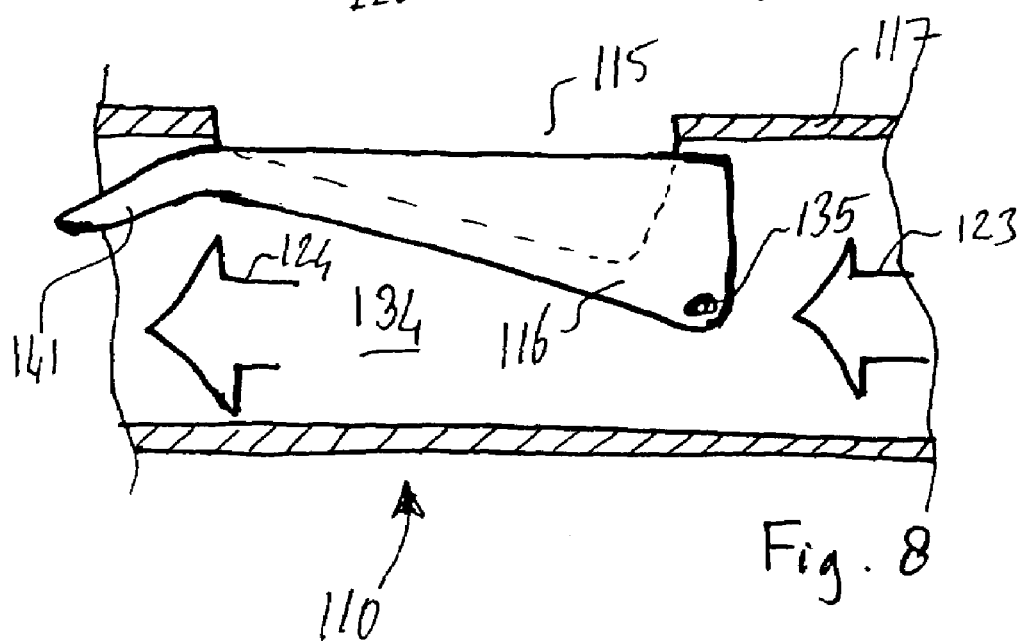
FIG. 8 is a view according to FIG. 7 but in a different operating condition.

In the embodiment shown in FIGS. 7 and 8, an opening 115 is provided in a wall 117 of the catheter 110 in essentially the same position as the opening 15 shown in FIGS. 1 and 2.

The valve body 116 is formed by a plate-shaped member forming approximately a segment of a circle when seen in frontal view. When in the inlet position, the valve body 116 extends closely along and inside a projection of the wall 117 in the area of the opening 115 (FIG. 8). Furthermore, the valve body 116 has a deflector 141 projecting into the lumen 134 on a proximal side of the valve body 116. When in the outlet position the valve body 116 extends diagonally across a section of said lumen 134 in the area of the outlet opening 115 (FIG. 7). The valve body 116 is pivotable between the inlet position and the outlet position and is hinged to the wall 117 about an axis 135 closely adjacent a distal end portion of the opening 115.

When the displacement device 6 is operative for drawing blood in proximal direction—as indicated by arrows 123, 124 in FIG. 8—the valve body 116 is urged and retained in its inlet position by the forces exerted by the flow onto the inside of the valve body 116. In order to counteract a pressure drop from the aorta 2 to the interior of the catheter 110, the deflector 141 causes an additional closing force exerted onto the valve body 116. Due to the large distance between the deflector 141 and the pivoting axis 135 where the valve body 116 is hinged to the wall 117, the deflector 141 causes the generation of a substantial closing torque about the axis 135.

When the operation of the displacement device is reversed causing the blood flow to be reversed as well, the blood flow (indicated by arrow 129) hitting the deflector 141 causes the valve body 116 to be opened. The pressure drop over the valve body 116 from the proximal side to the distal side, which is subsequently caused, causes the valve body 116 to be retained in the outlet position as long as the flow 129 is maintained.

From the above description, it will be apparent to the skilled person, that the present invention can be embodied in many alternative ways other than those described and mentioned above. It is for instance possible to directly mount the valve body in the catheter without the use of a fitting. Other exemplary alternatives are to provide the valve body in the form of a flap connected to the catheter wall or to the wall of a fitting by a flexible connection or to provide that the valve body is guided for translatory movement between the inlet position and the outlet position.

In the use of the catheter pump shown in FIG. 9 pulsations are generated in the blood flow in the aorta 2. In this example, a heart lung machine 43 including a pump 44 and an oxygenator 45 maintains the blood circulation in the patient. The blood flow 46 from the heart lung machine 43 to the patient is essentially non-pulsatile, because the oxygenator absorbs any pulsations caused by the pump 44. This essentially non-pulsatile blood flow 46 enters the aorta 2 closely adjacent the heart 1 which has been made deactivated.

The catheter 10 of the catheter pump 5 is inserted into the aorta 2 of a patient in a position having a distal end portion 12 in the aorta 2 of the patient.

The displacement device 6 connected to a proximal end 47 of the catheter 10 alternatingly withdraws blood from the aorta 2 and feeds blood to the aorta 2 via the catheter 10, such that pressure pulsations are generated in the area of the distal end portion 12 of the catheter 5. The displacement device 6 preferably has a stroke of 10–40 ml and is preferably constructed from a transparent polymer such as PC, PMMA or MEBS. For driving the displacement device 6 a commercially available drive system can be employed, for instance a conventional balloon pump.

The pulsations in the blood pressure pass into the arteries 48, 49, 50, 51 towards the bowels, the liver and the kidneys. Such local blood pressure pulsations have a positive effect on the organ perfusion (for instance expressed as a flow rate per unit of mass of organ tissue), which is believed to be caused by increased effective organ perfusion pressure differentials. A particular advantage of applying the pulsations as blood pressure pulsations directly in the aorta is, that the magnitude of the pulsations is large in the area of the arteries 48–51 towards the abdominal organs where the pulsating effect is desired. By applying the pulsations in the area of the carotid arteries 60, 61 leading towards the head, brain perfusion can be improved particularly effectively.

Moreover, since the pulsations are generated in the aorta 2, i.e. in an area downstream of and remote from the oxygenator 45, the pulsations do not interference significantly with the operation of the oxygenator.

To achieve particularly positive control over the pulsations in the arteries 48–51 towards the organs, the distal end portion 12 of the catheter 10 is positioned in a portion of the aorta 2 downstream of an area where the subclavian arteries 41, 42 connect to the aorta 2.

More specifically, control over the pulsations in the arteries 48–51 towards the organs is further enhanced since the distal end portion 12 of the catheter 10 is positioned in a portion of the aorta 2 where arteries 48–51 towards the organs connect to the aorta 2. In this example the area where the peak pressures in the pulsations are applied is formed by the outflow opening 15 in a fitting 14, which outflow opening 15 is preferably located between the junctions where arteries 48–51 towards the organs connect to the aorta, when the catheter is in its operating position inserted in a patient. The fitting 14 is preferably of the same type as the fitting 14 shown in FIGS. 3–6.

In the present example, the catheter 10 is inserted into the aorta 2 via an artery 52 in the area of the groin. In this location, a relatively large artery extends closely under the skin and can easily be reached. In combination with heart surgery, a particular advantage of this location of insertion of the catheter 10 compared with other locations, which in principle are conceivable as well, is that the catheter does not form an obstacle interfering with surgical manipulations in the area of the heart. An advantage of entry in the area of the groin compared with entry at the position where the blood flow 46 enters the body is that the catheter does not reduce the effective cross-sectional area available for the blood flow 46.

In the present example, the fluid that is displaced to and fro in the catheter 10 is blood from the patient. In principle, it is also possible to transfer the pulsations applied by the displacement device 6 (which is similar to the device described with reference to FIGS. 1 and 2) using another fluid such as air or a liquid. However, this presently appears to require either a sealing in the catheter or an inflatable body in the aorta 2, which would reduce the cross-sectional area of the aorta 2 available for blood flow.

The catheter 10 has a channel 53 communicating with its distal end portion 12 for alternatingly passing a fluid in a direction away from the distal end portion 12 towards the proximal end portion 47 and in a direction away from the proximal end portion 47 towards the distal end portion 12 and a connection at the proximal end 47 for coupling the catheter 10 to the displacement device 6 for alternatingly applying suction for displacing fluid from the catheter 10 to the displacement device 6 and for applying pressure for displacing fluid from the displacement device 6 to the catheter 10.

The desired location of the end portion of the catheter 10 is preferably achieved by suitably dimensioning the catheter 10. The distance between the position where the catheter enters the body and the displacement device 6 should preferably be fairly small, for instance 5 to 15 cm.

The catheter 10 according to FIG. 9 has an inlet passages 13 and an outlet passage 15 proximally spaced from the inlet passage, and a valve arrangement (see FIGS. 3–6) for obstructing outward blood flow via the inlet passages 13 and inward blood flow via the outlet passages 15. This provides the advantage that the pressure reduction during intake of blood occurs at a distance upstream of the arteries 48–51 leading to the organs, so that it has relatively little influence on reducing blood flow towards the organs, while the peak pressures of the pulsations are applied closely adjacent the arteries 48–51 leading to the organs. Furthermore, the pulsations involve displacement of blood along the aorta 2, so that the reduction of its cross-section available for blood flow due to the presence of the catheter 10 is at least partially compensated by blood transport through the catheter 10.

The spacing between the inlet passages 13 and the outlet passage 15 is preferably at least 8 cm and more preferably at least 13 cm and preferably at most 25 cm and more preferably at most 20 cm.

To achieve the desired position of the outlet passage 15 between the junctions where the arteries 48–51 leading to the organs branch off from the aorta 2 and while obtaining a suitable clearance between the displacement device 6 and the groin where the catheter 10 enters the patient, the proximal end 47 is preferably spaced 20 to 40 cm, measured along the catheter, from the outlet passage 15. To achieve the desired position of the distal tip, the catheter 10 preferably has a length measured from a distal tip to the proximal end 47 of at least 35 cm. For applying the pulsations in the arteries leading to the abdominal organs, the catheter preferably has a length of at most 50 cm.

To provide on the one hand a sufficiently large cross-section for fluid displacement through the catheter, while on the other hand allowing easy insertion of the catheter and sufficient remaining room for blood flow through the artery 52 through which the catheter 10 is inserted, the catheter 10 preferably has an external diameter of at least 4–5 mm and at most 6–7 mm. The optimal diameter will vary from patient to patient.

It is also possible to provide the catheter 10 with a locally reduced cross-section in a portion 63 of the catheter, which is located in the artery 52 in the groin area when the catheter 10 is in operative position inserted in the patient. The area having a reduced cross-section is preferably located in the most proximal 15 to 25 cm of the catheter.

The catheter has a filament (e.g. fiber or wire) reinforced wall and has a thickness of 0.2 to 0.5 mm. This small wall thickness is advantageous for obtaining a large internal cross-sectional area of the catheter channel 53 combined with a small outer cross-sectional area for easy entry of the catheter 10 while the fiber reinforcement provides sufficient stiffness for easy insertion and effective pressure pulse transfer from the displacement device 6 to the distal end 12 of the catheter 10.

The drive structure including the displacement device 6 and the drive system for driving the displacement device 6 and the catheter are preferably adapted for generating a maximum drive pressure of at least 300 mmHg and preferably at least 400 mmHg and at most about 600 mmHg. At such pressures, sufficient flow is generated to create effective pulsations while blood cell damage due to excessive shear stresses are avoided.

FIG. 10 illustrates the same treatment as FIG. 9, but employing a different catheter pump 305 having a different catheter 310. The catheter 310 shown in FIG. 10 has separate one-way check valves 354, 355, one at an inlet passage 313 and the other one at an outlet passage 315.

In FIG. 11 the same treatment is shown as in FIG. 9, but employing yet another catheter pump 405 having a different catheter 410. The catheter shown in FIG. 11 has inlet/outlet passages 413 and a channel 453 extending in longitudinal direction through the catheter 410. The channel 453 is adapted for providing continuously open communication of the displacement structure 406 with the blood in the aorta 2 via the inlet/outlet passages 413 for alternatingly displacing blood in and out via the inlet/outlet passages 413. This allows a particularly simple construction of the catheter, since the channel 453 and the inlet/outlet passages 413 are free of valves. The absence of valves, in turn, reduces the risk of occurrence of thrombosis, increases the simplicity and the reliability of the catheter construction and reduces the manufacturing costs of the catheter. The inlet/outlet passages 413 also form the passages via which blood is pressed into the aorta 2 for generating the desired pressure pulses.

It is observed that in the present examples, the catheter is shown in a treatment involving the deactivation of the heart and use of a heart lung machine. However, the proposed treatment using the proposed catheter and catheter pump can also be applied advantageously for the treatment of other indications such as during and after heart-lung machine assist (for instance in an intensive care unit) and during periods of unwanted hypotension (shock).

What is claimed is:

1. A catheter pump comprising:
a catheter having a distal end portion and a proximal end portion, and a channel communicating with said distal end portion for alternatingly passing a fluid in a direction away from said distal end portion towards said proximal end portion and in a direction away from said proximal end portion towards said distal end portion;
an inlet passage and an outlet passage proximally spaced at least 8 cm and at most 25 cm from said inlet passage,
a valve arrangement for at least restricting outward blood flow via said inlet passage and inward blood flow via said outlet passage;
a connection at said proximal end portion for coupling the catheter to a displacement structure; and
a displacement structure;
said displacement structure communicating with said catheter for alternatingly applying suction for displacing fluid from said catheter to said displacement structure and applying pressure for displacing fluid from said displacement structure to said catheter; and
said catheter being dimensioned for positioning said distal end portion in the aorta of a human patient.

2. A catheter pump comprising:
a catheter having a distal end portion and a proximal end, and a channel communicating with said distal end portion for alternatingly passing a fluid in a direction away from said distal end portion towards said proximal end and in a direction away from said proximal end towards said distal end portion;
an inlet passage and an outlet passage proximally spaced from said inlet passage and spaced 20 to 40 cm, measured along said catheter, from said proximal end;
a valve arrangement for at least restricting outward blood flow via said inlet passage and inward blood flow via said outlet passage;
a connection at said proximal end for coupling the catheter to a displacement structure; and
a displacement structure;
said displacement structure communicating with said catheter for alternatingly applying suction for displacing fluid from said catheter to said displacement structure and applying pressure for displacing fluid from said displacement structure to said catheter; and said catheter being dimensioned for positioning said distal end portion in the aorta of a human patient.

3. A catheter pump comprising:

a catheter having a distal end portion and a proximal end portion, and a channel communicating with said distal end portion for alternatingly passing a fluid in a direction away from said distal end portion towards said proximal end portion and in a direction away from said proximal end portion towards said distal end portion;

a connection at said proximal end portion for coupling the catheter to a displacement structure; and a displacement structure;

said displacement structure communicating with said catheter for alternatingly applying suction for displacing fluid from said catheter to said displacement structure and applying pressure for displacing fluid from said displacement structure to said catheter; and said catheter being dimensioned for positioning said distal end portion in the aorta of a human patient and comprising an inlet passage and a channel extending in longitudinal direction through the catheter, which channel is adapted for providing continuous fully open communication of said displacement structure via said inlet passage for alternatingly displacing fluid in and out via said inlet passage.

4. A catheter pump according to claim 3, having a length measured from a distal tip to the proximal end of at least 35 cm and at most 50 cm.

5. A catheter pump comprising:

a catheter having a distal end portion and a proximal end portion, a channel communicating with said distal end portion for alternatingly passing a fluid in a direction away from said distal end portion towards said proximal end portion and in a direction away from said proximal end portion towards said distal end portion;

a connection at said proximal end portion for coupling the catheter to a displacement structure; and a displacement structure;

said displacement structure communicating with said catheter for alternatingly applying suction for displacing fluid from said catheter to said displacement structure and applying pressure for displacing fluid from said displacement structure to said catheter; and said catheter being dimensioned for positioning said distal end portion in the aorta of a human patient and having a catheter wall including at least one reinforcement filament and having a thickness of at most 0.5 mm.

6. A catheter pump comprising:

a catheter having a distal end portion and a proximal end portion, and a channel communicating with said distal end portion for alternatingly passing a fluid in a direction away from said distal end portion towards said proximal end and in a direction away from said proximal end towards said distal end portion;

an inlet passage and an outlet passage proximally spaced from said inlet passage;

a valve arrangement for at least restricting outward blood flow via said inlet passage and inward blood flow via said outlet passage;

a connection at said proximal end portion for coupling the catheter to a displacement structure; and a displacement structure;

said displacement structure communicating with said catheter for alternatingly applying suction for displacing fluid from said catheter to said displacement structure and applying pressure for displacing fluid from said displacement structure to said catheter;

said catheter being dimensioned for positioning said distal end portion in the aorta of a human patient; and said valve arrangement including a valve body movable between an inlet position at least restricting flow through said outlet passage and allowing flow through said inlet passage and an outlet position at least restricting flow through said inlet passage and allowing flow through said outlet passage, further comprising a wall bounding a lumen, wherein said outlet passage is formed by an opening in said wall; and said valve body:

is a plate-shaped member, when in said inlet position, extends closely along and inside a projection of said wall in the area of said outlet opening, when in said outlet position, extends transversely across a section of said lumen on a distal side of said outlet opening, and is pivotable between said inlet position and said outlet position about an axis extending across a central portion of said lumen and centrally located behind said outlet opening.

7. A catheter pump according to claim 6, wherein said lumen has a round cross section;

said outlet opening is round in a view frontal thereto and wedge-shaped in a side view perpendicular to said frontal view; and said plate-shaped member is curved about an axis of curvature transverse to said pivoting axis, round in frontal view and wedge-shaped in a side view perpendicular thereto.

8. A catheter pump according to claim 7, wherein, in side view, opposite sides of said wedge shapes of said outlet opening and of said valve body extend at an angle of 75–50 to each other.

9. A catheter pump according to claim 7, wherein, in said inlet position, said valve body has a frontal projected area having a first portion on a proximal side of said pivoting axis and a second portion on a distal side of said pivoting axis, said first portion being larger than said second portion.

10. A catheter pump according to claim 6, wherein, in said outlet position, said valve body has a frontal projected area having a first portion on a side of said pivoting axis where said outlet opening is located and a second portion on an opposite side of said pivoting axis, said first portion being larger than said second portion.

11. A catheter pump according to claim 10, wherein said pivoting axis extends across said lumen, and wherein said lumen has a cross-sectional area having a portion on a side of said pivoting axis where said outlet opening is located and a portion on an opposite side of said axis, said portion on said side of said pivoting axis where said opening is located being larger than said portion on said opposite side of said pivoting axis.

12. A catheter pump comprising:

a catheter having a distal end portion and a proximal end portion, and a channel communicating with said distal end portion for alternatingly passing a fluid in a direction away from said distal end portion towards said proximal end and in a direction away from said proximal end towards said distal end portion;

an inlet passage and an outlet passage proximally spaced from said inlet passage;

a valve arrangement for at least restricting outward blood flow via said inlet passage and inward blood flow via said outlet passage;

a connection at said proximal end portion for coupling the catheter to a displacement structure; and a displacement structure;

said displacement structure communicating with said catheter for alternatingly applying suction for displacing fluid from said catheter to said displacement structure and applying pressure for displacing fluid from said displacement structure to said catheter;

said catheter being dimensioned for positioning said distal end portion in the aorta of a human patient; and said valve arrangement including a valve body movable between an inlet position at least restricting flow through said outlet passage and allowing flow through said inlet passage and an outlet position at least restricting flow through said inlet passage and allowing flow through said outlet passage;

further comprising a wall bounding a lumen, wherein said outlet passage is formed by an opening in said wall; and said valve body:

is a plate-shaped member, when in said inlet position, extends closely along and inside a projection of said wall in the area of said outlet opening, has a deflector projecting into said lumen from a proximal side of said valve body, when in said outlet position, extends diagonally across a section of said lumen in the area of said outlet opening, is pivotable between said inlet position and said outlet position, and is hinged to said wall in an area closely adjacent a distal end portion of said outlet opening.

13. A catheter pump comprising:

a catheter having a distal end portion and a proximal end portion, and a channel communicating with said distal end portion for alternatingly passing a fluid in a direction away from said distal end portion towards said proximal end portion and in a direction away from said proximal end portion towards said distal end portion;

a connection at said proximal end portion for coupling the catheter to a displacement structure; and a displacement structure;

said displacement structure communicating with said catheter for alternatingly applying suction for displacing fluid from said catheter to said displacement structure and applying pressure for displacing fluid from said displacement structure to said catheter;

said catheter being dimensioned for positioning said distal end portion in the aorta of a human patient; and said displacement structure and said catheter being adapted for generating maximum drive pressure in the area of said distal end portion of at least 100 mmHg and at most 500 mmHg.

14. A catheter pump according to claim 13, wherein said displacement structure is adapted for generating a maximum drive pressure of at least 300 mmHg and at most 600 mmHg.

15. A method for generating pulsations in the blood flow towards the organs of a patient including:

inserting a catheter into the aorta of a patient and bringing the catheter in a position having a distal end portion in the aorta of the patient; and alternatingly withdrawing fluid from the aorta and feeding fluid to the aorta via said catheter, such that pressure pulsations are generated in an area of the aorta where the distal end portion of the catheter is located;

wherein said distal end portion is positioned in a portion of the aorta downstream of an area where subclavian arteries connect to the aorta.

16. A method according to claim 15, wherein said distal end portion is positioned in a portion of the aorta where arteries leading from the aorta to at least one of the abdominal organs connect to the aorta.

17. A method according to claim 16, wherein said catheter is inserted into the aorta via an artery in the area of the groin.

* * * * *

UNITED STATES PATENT AND TRADEMARK OFFICE
CERTIFICATE OF CORRECTION

PATENT NO. : 6,974,409 B2  Page 1 of 1
DATED : December 13, 2005
INVENTOR(S) : Gijsbertus Jacob Verkerke, Arjan van der Plaats and Gerhard Rakhorst It is certified that error appears in the above-identified patent and that said Letters Patent is hereby corrected as shown below:

Column 12,
Line 35, delete "50" and insert -- 105° --.

Signed and Sealed this

Twenty-eighth Day of March, 2006

JON W. DUDAS
*Director of the United States Patent and Trademark Office*